United States Patent [19]

Carson et al.

[11] 4,207,237
[45] Jun. 10, 1980

[54] PREPARATION OF PYRROLE-2-ACETATES

[75] Inventors: John R. Carson; Richard J. Carmosin, both of Norristown; Anthony T. Stefanski, Bethlehem, all of Pa.

[73] Assignee: McNeilab, Inc., Fort Washington, Pa.

[21] Appl. No.: 951,440

[22] Filed: Oct. 16, 1978

Related U.S. Application Data

[63] Continuation-in-part of Ser. No. 789,310, Apr. 20, 1977, abandoned.

[51] Int. Cl.$^2$ ............................................. C07D 207/32
[52] U.S. Cl. ................................. 260/326.2; 260/326.47
[58] Field of Search ......................... 260/326.2, 326.47

[56] References Cited

U.S. PATENT DOCUMENTS

| | | | |
|---|---|---|---|
| 3,393,201 | 7/1968 | Preau | 260/326.2 |
| 3,544,589 | 12/1970 | Orth | 260/326.2 |
| 3,803,169 | 4/1974 | Carson | 260/326.2 |
| 3,957,818 | 5/1976 | Carson | 260/326.2 |
| 3,998,844 | 12/1976 | Carson | 260/326.2 |

OTHER PUBLICATIONS

Maffei; Gazzetta Chimica Italiana, vol. 76, pp. 345–351 (1946).
Chem. Abs., vol. 42, 1266 (1948).
Payer, Chem. Reviews, vol. 63, pp. 490–493, 497–498 (1963).

*Primary Examiner*—Mary C. Lee

[57] ABSTRACT

Loweralkyl 1-methylpyrrole-2-acetates are prepared by the reduction of loweralkyl α-imino-1-methylpyrrole-2-acetates using sodium dithionite as the reducing agent.

6 Claims, No Drawings

PREPARATION OF PYRROLE-2-ACETATES

CROSS-REFERENCE TO RELATED APPLICATION

This is a continuation-in-part application of our copending application Ser. No. 789,310, filed Apr. 20, 1977, now abandoned.

DESCRIPTION OF THE PREFERRED EMBODIMENT

This invention relates to a novel process of preparing loweralkyl 1-methylpyrrole-2-acetates of the formula:

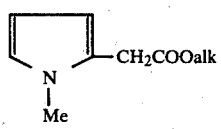
(I)

wherein alk is loweralkyl, preferably ethyl.

According to the instant process, an appropriate loweralkyl α-imino-1-methylpyrrole-2-acetate of formula (II), wherein alk is as previously defined and R is a member selected from the group consisting of hydrogen, loweralkyl, cycloalkyl, phenyl and phenyl substituted with from one to three substituents each selected from the group consisting of loweralkyl, loweralkyloxy and halo, is reduced to a corresponding loweralkyl 1-methylpyrrole-2-acetate of formula (I) by the action of sodium dithionite as the reducing agent.

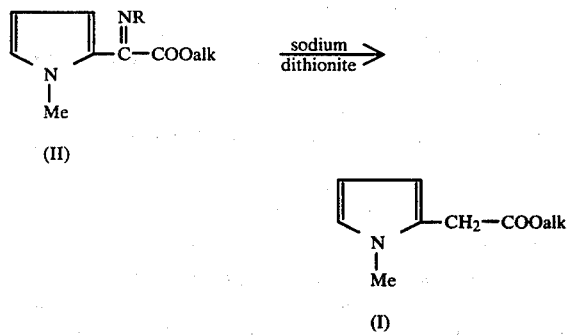

As used herein, "loweralkyl" refers to straight or branched chained alkyls having from 1 to 6 carbons, for example, methyl, ethyl, propyl, isopropyl, butyl, tert-butyl, pentyl, hexyl and the like; "halo" refers to chloro, bromo, fluoro and iodo; and "cyclohexyl" refers to cyclopentyl and cyclohexyl.

The reduction reaction may be performed at reaction temperatures varying from about 0° C. to about 50° C. in, preferably, aqueous acetic acid using a stoichiometric excess of sodium dithionite as the reducing agent.

The loweralkyl 1-methylpyrrole-2-acetates of formula (I) have been reported in the literature as being useful intermediates in the preparation of 5-aroyl-pyrrole-2-acetic acid derivatives having anti-inflammatory activity (e.g., see U.S. Pat. Nos. 3,752,826; 3,803,169; 3,846,447; and 3,957,818).

The α-imino-acetate precursors of formula (II) are obtainable by several methods. For example, by reacting a loweralkyl 1-methylpyrrole-2-glyoxylate of formula (III), wherein alk is as previously defined, with an appropriate phenylamine of formula (IV), wherein n is an integer from 0 to 3 and each X is a member selected from the group consisting of hydrogen, loweralkyl, loweralkyloxy and halo, the corresponding α-imino-acetates of formula (II) wherein R is phenyl or substituted phenyl are obtained (II-a). The reaction may be conducted in an anhydrous inert organic solvent, such as, for example, the aromatic hydrocarbons and halocarbons previously described and, preferably, under reflux conditions with azeotropic removal of water formed during the course of the reaction. The presence of a catalytic amount of a strong acid, e.g., an organic acid such as toluenesulfonic acid, methanesulfonic acid and the like or a mineral acid such as $H_2SO_4$, HCl and the like, may be employed to enhance the rate of reaction.

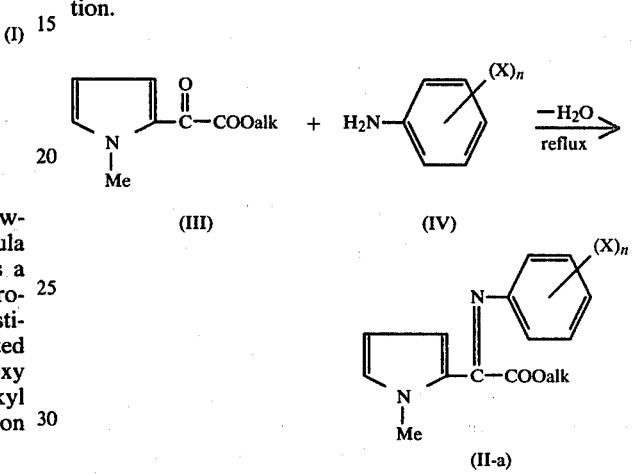

The α-imino-acetates of formula (II) wherein R is loweralkyl or cycloalkyl (II-b) may be prepared by reacting the glyoxylate of formula (III) with a stoichiometric excess of an appropriate alkylamine of formula (V), wherein Y is a member selected from the group consisting of loweralkyl and cycloalkyl, in an aprotic organic solvent under an inert atmosphere, e.g., nitrogen, argon and the like, and in the presence of titanium tetrachloride. At least six molar equivalents of (V) to one molar equivalent of (III) is preferred. Suitable solvents include aromatic hydrocarbons, e.g., benzene, toluene, xylene and the like; ethers, e.g., diethyl ether, dioxane, tetrahydrofuran and the like; and halogenated hydrocarbons, e.g., methylene dichloride, chloroform and the like. The reaction is preferably conducted in the cold, e.g., at temperatures from about −20° C. to about 10° C.

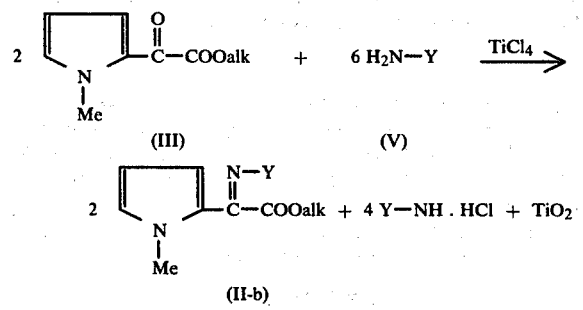

The α-imino-acetates of formula (II) wherein R is hydrogen may be prepared by the interaction of N-methylpyrrole (VI) and loweralkyl cyanoformate (VII) in the presence of hydrogen chloride under Houben Hoesch reaction conditions. In general, dry HCl gas is bubbled through a solution of (VI) and (VII) in an aprotic organic solvent suitable for Houben Hoesch reactions, e.g., ethers, halogenated hydrocarbons, aromatic hydrocarbons, and the like. Alternatively, an ethereal solution of HCl is slowly added to the solution of (VI) and (VII). The resultant loweralkyl α-imino-1-methylpyrrole-2-acetate HCl salt (VIII) is transformed to the corresponding free imino state (II-c) by treatment with at least an equivalent amount of a suitable base, e.g., an alkali metal carbonate or bicarbonate, or a liquid amine which can serve as a halogen acid acceptor such as pyridine, triethylamine and the like.

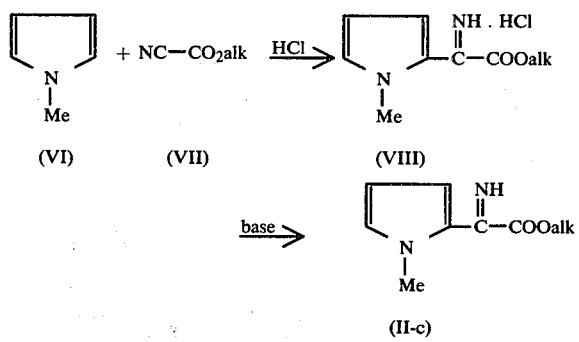

The loweralkyl 1-methylpyrrole-2-glyoxylates of formula (III) may be prepared according to the method described by A. Treibs and F. H. Kreuzer, Ann., 721, 105 (1969). The loweralkyl cyanoformates of formula (VII) may be prepared in accordance with the method described by M. E. Childs and W. P. Weber, J. Org. Chem., 41, 3486 (1976).

The α-imino-acetates of formulas (II-a), (II-b) and (II-c), collectively represented by formula (II), are subsequently reduced to the desired loweralkyl 1-methylpyrrole-2-acetates of formula (I) using sodium dithionite as the reducing agent.

EXAMPLE I

A. Ethyl α-imino-1-methylpyrrole-2-acetate

A stream of dry halogen chloride is passed as a moderate rate through a solution of 12.5 g of N-methylpyrrole and 16.8 g of ethyl cyanoformate in 125 mls of ethanol-free chloroform at 22° C. for 3½ hours. The reaction mixture is added dropwise with stirring to a 1.5 liter solution of 5% sodium bicarbonate. The chloroform layer is separated, dried over Na$_2$SO$_4$ and evaporated in vacuo at room temperature to give a brown oil (ethyl α-imino-1-methylpyrrole-2-acetate).

B.

The procedure of Example I-A is followed except that an equivalent amount of methyl cyanoformate and n-butyl cyanoformate are substituted for the ethyl cyanoformate used therein to yield, as respective products:

methyl α-imino-1-methylpyrrole-2-acetate; and n-butyl α-imino-1-methylpyrrole-2-acetate.

EXAMPLE II

A. Ethyl α-imino-1-methylpyrrole-2-acetate hydrochloride

A stream of dry hydrogen chloride is bubbled slowly into a solution of 2.7 g of ethyl cyanoformate and 2.0 g of N-methylpyrrole in 20 ml of ethanol-free chloroform at 22° C. for 5¾ hrs. The imine hydrochloride is measured by hydrolyzing for 30 mins with water and determining the hyrolysis product, ethyl 1-methylpyrrole-2-glyoxylate, gas chromatographically with internal standard. A 75% yield is measured.

B.

Following the procedure above but substituting toluene and tetrahydrofuran for chloroform, yields of 65% and 70%, respectively, are obtained.

EXAMPLE III

Ethyl α-(4-methoxyphenylimino)-1-methylpyrrole-2-acetate

To a solution of 4.0 g ethyl 1-methylpyrrole-2-glyoxylate and 2.96 g p-anisidine in 20 ml toluene is added 24 mg p-toluenesulfonic acid. Heating at reflux for 4 days with water being removed with a Dean-Stark trap is followed by washing successively with aqueous hydrochloric acid, aqueous sodium bicarbonate and brine. After drying, evaporation of the solvent affords a dark solid. Recrystallization from isopropanol gives a 58% yield of ethyl α-(4-methoxyphenylimino)-1-methylpyrrole-2-acetate, m.p. 83°–85° C.

EXAMPLE IV

Ethyl α-cyclohexylimino-1-methylpyrrole-2-acetate

To a solution of 25 g ethyl 1-methylpyrrole-2-glyoxylate and 44.5 g cyclohexylamine in 700 ml ether under nitrogen at 0° C. is added 8.8 ml of titanium tetrachloride in 80 ml pentane. After stirring at room temperature overnight, the precipitate is removed by filtration. The filtrate is evaporated and the resulting oil distilled. The fraction collected at 111°–117° C. (5 millitorr) is crystallized from hexane to afford a 15% yield of ethyl α-cyclohexylimino-1-methylpyrrole-2-acetate, m.p. 35°–36° C.

EXAMPLE V

Ethyl α-phenylimino-1-methylpyrrole-2-acetate

To a solution of 4.0 ethyl 1-methylpyrrole-2-glyoxylate and 2.23 g aniline in 20 ml toluene is added 30 mg p-toluenesulfonic acid. Heating at reflux for 2 days with water being removed with a Dean-Stark trap is followed by dilution with ether. The precipitate is removed by filtration and the filtrate washed successively with aqueous hydrochloric acid, aqueous sodium bicarbonate and brine. After drying, the solvent is evaporated to afford a residue which is recrystallized twice from isopropanol to give a 43% yield of ethyl α-phenylimino-1-methylpyrrole-2-acetate, m.p. 69°–71° C.

EXAMPLE VI

Ethyl 1-methylpyrrole-2-acetate

Three equivalents of sodium dithionite (0.36 g) is added in one portion with vigorous stirring to a solution of 0.2 g ethyl α-(4-methoxyphenylimino)-1-methylpyrrole-2-acetate in 6 ml glacial acetic acid plus 2.5 ml water. After ten minutes two additional equivalents of dithionite is added. After 10 mins more, a sufficient sample for G.C. analysis is poured into ice and extracted with chloroform. Analysis by gas chromatography (G.C.) with an internal standard measures 34% ethyl 1-methylpyrrole-2-acetate.

EXAMPLE VII

By following the reduction procedure of Example VI, except that an equivalent amount of each of the imino-pyrroles obtained in Example I is used as the precursor to be reduced, the respective loweralkyl 1-methylpyrrole-2-acetates are obtained.

EXAMPLE VIII

A.

By following the procedure of Example III, except that an equivalent amount of 4-chloroaniline, 4-ethoxyaniline, 2-bromo-4-ethylaniline, 2,4-dimethoxyaniline, 2,4,6-trimethylaniline and 2,4,6-trichloroaniline are substituted for the p-anisidine used therein, the following respective products are obtained:
ethyl α-(4-chlorophenylimino)-1-methylpyrrole-2-acetate;
ethyl α-(4-ethoxyphenylimino)-1-methylpyrrole-2-acetate;
ethyl α-(2-bromo-4-ethylphenylimino)-1-methylpyrrole-2-acetate;
ethyl α-(2,4-dimethoxyphenylimino)-1-methylpyrrole-2-acetate;
ethyl α-(2,4,6-trimethylphenylimino)-1-methylpyrrole-2-acetate; and
ethyl α-(2,4,6-trichlorophenylimino)-1-methylpyrrole-2-acetate.

B.

Each of the foregoing α-imino-acetates may be reduced to ethyl 1-methylpyrrole-2-acetate according to the procedure of Example VI using sodium dithionite as the reducing agent.

EXAMPLE IX

A.

The procedure of Example IV is repeated except that an equivalent quantity of n-butylamine and cyclopentylamine is substituted for the cyclohexylamine use therein to yield, as respective products:
ethyl α-n-butylimino-1-methylpyrrole-b 2-acetate; and
ethyl α-cyclopentylimino-1-methylpyrrole-2-acetate.

B.

Reduction of each of the foregoing α-imino-acetates to ethyl 1-methylpyrrole-2-acetate with sodium dithionite as the reducing agent may be carried out according to the procedure of Example VI.

We claim:

1. A process of preparing a loweralkyl 1-methylpyrrole-2-acetate which comprises reducing a loweralkyl α-imino-1-methylpyrrole-2-acetate having the formula:

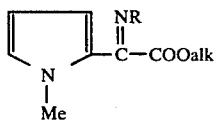

wherein: alk is loweralkyl; and
R is a member selected from the group consisting of hydrogen, loweralkyl, cyclopentyl, cyclohexyl, phenyl and phenyl substituted with from one to three substituents each selected from the group consisting of loweralkyl, loweralkyloxy and halo; by the action of sodium dithionite as the reducing agent.

2. A process of preparing ethyl 1-methylpyrrole-2-acetate which comprises reducing an ethyl α-imino-1-methylpyrrole-2-acetate having the formula:

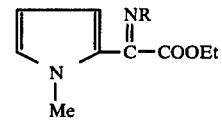

wherein:
R is a member selected from the group consisting of hydrogen, loweralkyl, cyclopentyl, cyclohexyl, phenyl and phenyl substituted with from one to three substituents each selected from the group consisting of loweralkyl, loweralkyloxy and halo; by the action of sodium dithionite as the reducing agent.

3. A process of preparing ethyl 1-methylpyrrole-2-acetate which comprises reducing ethyl α-(4-methoxyphenylimino)-1-methylpyrrole-2-acetate by the action of sodium dithionite as the reducing agent.

4. A process of preparing a loweralkyl 1-methylpyrrole-2-acetate which comprises reacting a loweralkyl α-imino-1-methylpyrrole-2-acetate having the formula:

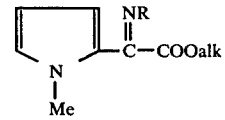

wherein:
alk is loweralkyl; and
R is a member selected from the group consisting of hydrogen, loweralkyl, cyclopentyl, cyclohexyl, phenyl and phenyl substituted with from one to three substituents each selected from the group consisting of loweralkyl, loweralkyloxy and halo; with a stoichiometric excess of sodium dithionite in aqueous acetic acid at about 0°–50° C.

5. A process of preparing ethyl 1-methylpyrrole-2-acetate which comprises reacting an ethyl α-imino-1-methylpyrrole-2-acetate having the formula:

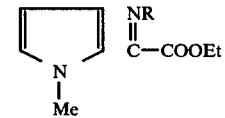

wherein:
R is a member selected from the group consisting of hydrogen, loweralkyl, cyclopentyl, cyclohexyl, phenyl and phenyl substituted with from one to three substituents each selected from the group consisting of loweralkyl, loweralkyloxy and halo; with a stoichiometric excess of sodium dithionite in aqueous acetic acid at about 50° C.

6. A process of preparing ethyl 1-methylpyrrole-2-acetate which comprises reacting ethyl α-(4-methoxyphenylimino)-1-methylpyrrole-2-acetate with a stoichiometric excess of sodium dithionite in aqueous acetic acid at about 50° C.

* * * * *